(12) United States Patent
Chin et al.

(10) Patent No.: US 8,021,860 B2
(45) Date of Patent: Sep. 20, 2011

(54) METHOD FOR PRODUCING HUMAN ANTIBODIES TO A SELF PHYSIOLOGICAL RECEPTOR BY SITE-DIRECTED IN VITRO IMMUNIZATION OF HUMAN LYMPHOCYTES

(76) Inventors: Li-Te Chin, Hsinchu (TW); Shu-Ching Hsu, Yanchao Township, Kaohsiung County (TW)

(*) Notice: Subject to any disclaimer, the term of this patent is extended or adjusted under 35 U.S.C. 154(b) by 149 days.

(21) Appl. No.: 12/318,679

(22) Filed: Jan. 6, 2009

(65) Prior Publication Data
US 2009/0286224 A1 Nov. 19, 2009

Related U.S. Application Data

(62) Division of application No. 10/866,120, filed on Jun. 14, 2004, now Pat. No. 7,494,779.

(51) Int. Cl.
*C12P 21/04* (2006.01)
(52) U.S. Cl. .................................. 435/70.4
(58) Field of Classification Search .............. None
See application file for complete search history.

(56) References Cited

U.S. PATENT DOCUMENTS

| 5,811,097 | A | 9/1998 | Allison et al. |
| 5,855,887 | A | 1/1999 | Allison et al. |
| 6,051,227 | A | 4/2000 | Allison et al. |
| 6,150,584 | A | 11/2000 | Kucherlapati et al. |
| 6,682,736 | B1 | 1/2004 | Hanson et al. |

FOREIGN PATENT DOCUMENTS

| WO | WO 00/37504 | 6/2000 |
| WO | WO 00/32231 | 8/2000 |
| WO | WO 01/14424 A2 | 1/2001 |

OTHER PUBLICATIONS

Peter S. Linsley, William Brady, Mrk Urnes, Laura S. Grosmaire, Nitin K. Damle, and Jeffrey A. Ledbetter; CTLA-4 Is a Second Receptor for the B Cell Activation Antigen B7; J. Exp. Med., vol. 174, Sep. 1991; pp. 561-569.

L.T. Chin, J. Hinkula, M. Levi, M. Ohlin, B. Wahren, C.A.K. Borrebaeck; Site-directed primary in vitro immunization: production of HIV-1 neutralizing human monoclonal antibodies from lymphocytes obtained from seronegative donors; Immunology, vol. 81, 1994; pp. 428-434.

Lie-Te Chin, Ann-Christin Malmborg, Karin Kristensson, Jorma Hinkula, Britta Wahren, and Carl A.K. Borrebaeck; Mimicking the humoral immune response in vitro results in antigen-specific isotype switching supported by specific autologous T helper cells: generation of human HIV-1 neutralizing IgG monoclonal antibodies form naive donors: Eur. J. Immunol.,1995; vol. 25, pp. 657-663.

Stephane Demotz, Antonio Lanzavecchia, Ulrich Eisel, Heiner Neimann, Christian Widmann, and Giampietro Corradin; Delineation of Several Dr-restricted Tetanus Toxin T Cell Epitopes; The Journal of Immunology, Jan. 15, 1989; vol. 142, No. 2, pp. 394-402.

Dana R. Leach, Matthew F. Krummel, James P. Allison; Enhancement of antitumor immunity by CTLA-4 blockade; Science, vol. 271Mar. 22, 1996; pp. 1734-1736.

*Primary Examiner* — Ilia Ouspenski
(74) *Attorney, Agent, or Firm* — Bacon & Thomas, PLLC

(57) ABSTRACT

A method for obtaining agonist, antagonist and inverse agonist, to a given physiological receptor is disclosed. For the method, use is made of in silico design synthetic immunogens, which are caused to act in vitro on human lymphocyte-containing cell populations. A preferred receptor is human CD152, particularly the regions of CDR1, CDR2 and CDR3 that elicit antibodies serving as antagonist, inverse agonist and agonist, respectively. Also provided is a method in the treatment of human peripheral lymphocytes for use in the screening of CD152 ligands that yield pharmacological effects.

6 Claims, 4 Drawing Sheets

1   MACLGFQRHK AQLNLATRTW PCTLLFFLLF IPVFCKAMHV AQPAVVLASS   50
51  RGIASFVCEY ASPGKATEVR VTVLRQADSQ VTEVCAA TYM MGNELTFLDD  100
101 SICTGTSSGN QVNLTIQGLR AMDTGLYICK VELMYPPPYY LGIGNGTQIY   150
151 VIDPEPCPDS DFLLWILAAV SSGLFFYSFL LTAVSLSKML KKRSPLTTGV   200
201 YVKMPPTEPE CEKQFQPYFI P I N                              223

Fig.1B

METHOD FOR PRODUCING HUMAN ANTIBODIES TO A SELF PHYSIOLOGICAL RECEPTOR BY SITE-DIRECTED IN VITRO IMMUNIZATION OF HUMAN LYMPHOCYTES

This application is a divisional application of U.S. patent application Ser. No. 10/866,120, filed on Jun. 14, 2004, the entire contents of which are herein incorporated by reference.

BACKGROUND OF THE INVENTION

1. Field of the Invention

The present invention relates to methods for producing complete human antibodies and, more particularly, to a method for producing human antibodies of agonist, antagonist and/or inverse agonist to a biological receptor and the antibodies produced by the same method.

2. Description of Related Art

Generally speaking, drugs must reach specific sites in the body to achieve pharmaceutical effects. Most of these sites are composed of cells that provide target molecules, i.e., receptors, to bind with, or interact with the molecules of drugs. The drug-receptor interaction or binding may lead to either an activation of the receptor, which ultimately results in a biological response; or a blockade of the receptor, which hinder the receptor activation by other drugs or ligands. Pharmacodynamics thus defines an agonist as a drug has the same or similar effect as a group of drugs or ligands. Accordingly, when a drug counteracts the effect of another drug or group of ligands, it is called an antagonist. In the situation where a ligand produces an effect opposite to that of the agonist by occupying the same receptor, it is called an inverse agonist.

Human antibodies have been successfully used for therapeutic drugs against various diseases. These diseases are traditionally infectious diseases, such as infections by respiratory syncytial virus (RSV). Recently, however, antibodies are increasingly used in the therapy of many other disorders, including autoimmune disorders and malignancies like metastastic breast cancer, non-Hodgkin's lymphoma, chronic lymphocytic leukemia and acute myeloid leukemia. Prophylactic use against organ rejection or blood clotting during angioplasty has also been achieved. In general, therapeutically monoclonal antibodies (MAbs) clinically available so far act by binding to ligands, e.g., virus or cytokines, thereby preventing their interactions with the respective receptors and thus blocking unwanted natural effector functions. Other existing receptor-specific monoclonal antibodies have been confined mostly to direct defensive and demolishing mechanisms to receptor-bearing targets such as malignant cells, thereby mediate their death. Although these systems have been extremely effective, they are not readily adapted to resolve more physiologic situation in which receptor-acting antibodies have pharmacodynamical activities.

While yet to be fully available, antibodies with a defined pharmacologic activity have been reported lately. For example, WO 00/32231, U.S. Pat. Nos. 5,811,097, 5,855,887 and 6,051,227 disclose MAbs to mouse CD152 (cytotoxic T lymphocyte antigen-4, CTLA-4) derived from hamsters immunized with a mouse CD152-human IgG1 fusion protein. As CD152 belongs to a groups of immunomodulating receptors that collectively termed as CD28 superfamily and represents a receptor negatively involved in T-lymphocyte co-stimulatory pathways regulating both humoral (antibody-mediated) and cellular immune response, an anti-tumor immune response that shows specificity and memory against the growing tumor was thereafter provoked by injecting antibodies specific for the receptor into mice with tumors (Leach et al., Science 271:1734, 1996). The idea behind this "CTLA-4 (antibody) blockade" approach is that the negative function of CD152 can be blocked with antibodies, therefore acting as antagonists, which may allow the activation or sustenance of residual but effective anti-tumor immunity.

Blocking the negative regulatory role for CD152 inhibition of the immune response provides a novel therapeutic technology, allowing the immune system to recognize and more vigorously attack foreign pathogens and cancers. However, antibodies with murine sequences often elicit immunological responses in the patient (human anti-mouse response) when administered to a human patient. Therefore, it is desirable to prepare fully human antibodies that are void of non-human sequences. By immunizing engineered transgenic mice harboring human immunoglobulin genes, fully human antibodies against CD152 have been reported (see, e.g., WO 00/37504, WO 01/14424, U.S. Pat. Nos. 6,150,584 and 6,682,736). The most exciting conclusion from continuous studies of these anti-CD152 blocking antibodies is the potential for antagonistic antibodies to strengthen the immune response against certain tumors and pathogens, leading to the reduction or elimination of well-established tumors as well as enhancement of antibody reaction to vaccinations.

Being an inhibitory receptor of the CD28 receptor family that plays a key role in regulating T cell activation, agonist binding to CD152 reduces T cell proliferation and cytokine production, resulting in attenuated immune responses. Endogenous agonists include CD80 and CD86 present on antigen-presenting cells (APCs) and CD152 ligation mediates tolerance and anergy. As shown by many and generally accepted, blockade of CD152-agonist interactions, provided by antagonistic antibodies, reduces the inhibition mediated through the CD152 signaling. However, comprehensive receptor-binding drugs should offer activities stopping the binding of the native agent without eliciting a response, i.e., antagonists; but also triggering the same or even opposite events as the native ligand, i.e., agonists or inverse agonists, respectively. In the case of CD152, the use of an agonist would therefore promote organ transplantation and blockade of autoimmune disease by the inhibitory costimulatory pathway. Clearly, it would offer solution to clinical conditions such as allergies, graft versus host disease and graft rejection. On the other hand, both designed and serendipitous inverse agonists could result in medications that display greater efficacy in cancer therapy.

Currently available anti-human CD152 huMAbs only act as antagonistic blocking agents have limited their usefulness in clinical applications. The present invention addresses needs for molecules having varied abilities to preferentially bind to and/or signal through CD152 receptor and methods of screening such molecules for selected and differential manipulation of T cell responses in vitro. Such human antibody molecules would be of beneficial use in a variety of applications, including, e.g., therapeutic and prophylactic treatments and vaccinations. The present invention fulfills these and other needs.

More details about the related prior art in this field can be found in the references listed below:

1. Chin L T, Hinkula J, Levi M, Ohlin M, Wahren B, Borrebaeck C A K. (1994) Site-directed primary in vitro immunization: Production of HIV-1 neutralizing human monoclonal antibodies from sero-negative donors. Immunology 81: 428-34.
2. Chin L T, Malmborg A C, Kristensson K, Hinkula J, Borrebaeck, C A K. (1995) Mimicking the humoral immune response in vitro results in antigen-specific isotype switching by autologous T helper cells. Eur. J. Immunol. 25:657-663.
3. Leach D R, Krummel M F, Allison J P. (1996) Enhancement of antitumor immunity by CTLA-4 blockade. Science. 271:1734-6.
4. Linsley P S, Brady W, Urnes M, Grosmaire L S, Damle N K, Ledbetter J A. (1991) CTLA-4 is a second receptor for the B cell activation antigen B7. J. Exp. Med. 174:561-9.
5. Demotz S, Lanzavecchia A, Eisel U, Niemann H, Widmann C, Corradin G. (1989) Delineation of several DR-restricted tetanus toxin T cell epitopes. J. Immunol. 142:394-402.

SUMMARY OF THE INVENTION

The object of the present invention is to provide a simple, effective method for producing human antibodies to a specific receptor, or the specific domains of the receptors without unwanted responses, such as human anti-mouse response (allergic responses).

Another object of the present invention is to provide a simple, effective method for producing agonist, antagonist and inverse agonist to a particular human CD152 receptor with less allergic response.

Another object of the present invention is to provide antibodies for being agonist, antagonist and inverse agonist to a specific receptor, especially to a human CD152 receptor.

Another object of the present invention is to a method for producing human antibodies to a specific receptor, or the specific domains of the receptors with less allergic responses.

Another object of the present invention is to a method for generating human antibodies that recognize at least three different antigenic sites of human CD152.

Another object of the present invention is to provide antigenic conjugate to provoke an antibody response with less allergic potential.

Another object of the present invention is to provide a simple method for identifying the pharmacological effects of an antibody for being agonist, antagonist, or inverse agonist to a receptor in vitro.

Another object of the present invention is to provide a method for constructing and predicting amino acid sequences of epitopes to provoke an antibody response in silico.

To achieve the objects, the method of the present invention for producing human antibodies of agonist, antagonist and/or inverse agonist to a receptor, comprising following steps: (a) defining peptide fragments resembling respective extracelluar domains of a receptor by the use of in silico characteristics of the respective extracellular domains of the receptor; (b) optionally defining amino acid sequences of coupled-fragments having the peptide fragments and a T-helper epitope by reassembling or coupling the peptide fragments and the T-helper in silico; wherein at least one T-helper is coupled with a peptide fragment; (c) preparing immunogens having amino acid sequences of the coupled-fragments; (d) stimulating human lymphocytes with the immunogens in vitro; (e) identifying and optionally screening the human lymphocytes that produce antibodies able to recognize the receptor; and (f) collecting the antibodies.

The antigenic conjugate of the present invention comprises coupled-fragments and optionally the induced antibodies thereof that specifically recognize a receptor; wherein the amino acid sequences of the coupled-fragments comprise a T-helper epitope and peptide fragments corresponding to the respective extracellular domains of the receptor.

The method of the present invention for identifying the pharmacological effects of an antibody for being agonist, antagonist, or inverse agonist to a receptor in vitro, comprising following steps: (a) providing human lymphocytes, a mitogen, a ligand, and optionally a polyclonal activator; (b) preparing plural mixtures of ligands and mitogens by adding mitogens or polyclonal activators to separate containers of increasing concentrations of the ligand; (c) providing a first control culture by adding mitogen only, and providing a second control culture by adding a natural agonist of the receptor; (d) inoculating human lymphocytes to the first control culture, the second control culture, and the plural mixtures of ligands and mitogens; (e) determining the degree of the programmed cell death (apoptosis) and/or proliferation in human lymphocytes in each culture and each mixture; and (f) determining the efficacy of the ligand to the receptor by the degree of the programmed cell death (apoptosis) and/or proliferation of mixtures of increasing concentrations of the ligand.

Generally, the present invention provides a method of epitope prediction from an amino acid sequence to find those likely to provoke an antibody response following in vitro stimulation. To this end, the extracellular domain where drugs and natural ligands act on was analyzed by using the following algorithms:
 (a) Chou-Fasman indices for the possible location of alpha ($\alpha$) helices, beta ($\beta$) sheets and beta turns;
 (b) Kyte and Doolittle for hydrophobicity;
 (c) Karplus and Schulz for flexibility; and
 (d) Surface probability The predicted antigenic regions were identified by locations adjacent to $\beta$-sheets or $\alpha$-helical structures and in regions of hydrophilicity and flexibility. Synthetic peptides composed of the predicted antigenic regions and a T-helper epitope from tetanus toxin QYIKANSKFIGITEL (Seq. ID No. 1) (Demotz et al., J. Immunol. 142:394, 1989), were evaluated in vitro by using human peripheral lymphocytes to assess immunological response.

After computer-aided in silico design of peptide-based immunogens was accomplished, lymphocytes from naive human donors are contacted in vitro with the synthetic antigens of interest, and cells that produce antibodies against the antigen are identified. Because the lymphocytes are immunized in vitro rather than in vivo, it is possible to control which antigen, or which part of the antigen, would be recognized by the antibody. Thus, this method is particularly useful in the preparation of antibodies against physiological important receptors such as CD152 that are inherently more difficult to perform immunization. Consistent with this, it has been shown in murine models that CD152-defective mice show extensive and lethal lymphadenopathy with T-cell infiltration of various tissues. Therefore it is impossible, even in principle, to obtain pre-existing antibody, let alone immunizing a human, to CD152 molecule. Accordingly, the present invention also provides a potential means both of percument the human antibody responses and unleaching the responses to nature occurring physiological receptors, which may not be recognized by donors' own immune system in vivo.

Structural analysis showed human CD152 to be most comparable to immunoglobulin superfamily variable domains, with eight $\beta$strands providing the framework for three complementary determining region-like loops, CDR1, CDR2 and CDR3. Preferred antigens derived from receptors are the complementary determining regions (CDRs) of CD152, or an immunogenic fragment thereof. More preferably, the immunogen (or antigen) is a peptide comprising one of the CDRs and the QYIKANSKFIGITEL (Seq. ID No. 1) T-helper epitope. In one aspect, the invention provides isolated or recombinant polypeptides comprising an extracellular domain sequence, said extracellular domain sequence having at least about 75% amino acid sequence identity to, or the full length sequence of, at least one of SEQ ID NOs: 2-7, and is not a naturally-occurring extracellular domain sequence because of T-helper epitope conjugation, and wherein said polypeptide has a CDR sequence of CD152.

In another aspect, the invention further provides a method of generating human antibodies that recognize at least three different antigenic sites of human CD152. Thus, by immunizing the lymphocytes with one antigen and screening the immunized lymphocytes with a recombinant CD152 antigen, fully human antibodies recognizing a physiological receptor can be obtained. It is common experience among practitioners in the art to prolong the ability of antibody production from EBV-transformed, human antibody-producing cultures by subjected to various further treatments. For example, the cells can be fused with heteromyeloma cells to form trioma cells, which can live a long time and stably produce antibodies. Various available recombinant methods can be applied to allow such antibodies also be produced in bacteria, yeast or mammalian cells.

Accordingly, a further aspect of the invention provides a method of preparing a fully human antibodies recognizing a physiological receptor, comprising:
(a) providing a group of lymphocytes obtained from a naive human donor;
(b) immunizing said lymphocytes with computer-aided in silico design antigens in vitro;
(c) adding Epstein-Barr virus (EBV) to the immunized lymphocytes;
(d) identifying EBV-infected cells that produce the antibody that recognizes the receptor; and
(e) screening the antibodies produced in step (d) for the presence of pharmacologic functions.

The method may further comprise the step of removing $CD8^+$ cells and $CD56^+$ cells from said lymphocytes prior to step (b). The $CD8^+$ and $CD56^+$ cells can be removed using any method established in the art. For example, these cells can be removed using antibodies that are specific for CD8 and CD56, respectively. In one embodiment, these antibodies are attached to magnetic beads. Additionally or alternatively, the method may further comprise forming trioma cells or recombinant immunoglobulin, and likewise, their respective fragments from step (d), thereby identifying complete human monoclonal antibodies. Alternatively, polyclonal antibodies can be prepared from a group of antibody-producing cells obtained using the present invention, which are not cultured as individual clones. The antibody preferably recognizes the antigen with a Kd of about 100 nM or less, about 30 nM or less, about 10 nM or less, about 3 nM or less, or about 1 nM or less. The antibody is preferably an IgG antibody, particularly IgG1 and IgG4.

The identifying or screening method may also use other mitogens or polyclonal activators, e.g., concanvalin A (Con A), pokeweed mitogen (PWM), phorbol 12-myristate 13-acetate (PMA) and the superantigen such as staphylococcal enterotoxin A (SEA), to replace or to use in conjugation with PHA therein.

In addition, the invention includes complete human antibodies prepared according to the methods of the invention. In particular, the antibodies can recognize respective specific regions on the extracellular domain of human CD152, such as the CDR regions, and preferably initiate pharmacodynamical effects on human peripheral blood mononuclear cells (PBMC) after engagement. Some such antibodies induce T-cell apoptosis, but do not induce proliferation, similar to that cause by natural agonist, i.e., CD80. In some embodiments, the apoptosis ameliorates and mediocre proliferation appears, which commonly found in an antagonist. Most importantly, other such antibodies modulate T-cell proliferation, but do not induce apoptosis of mitogen-stimulated human PBMC. This antibody may thus probably act as an inverse agonist. Pharmaceutical compositions comprising the antibodies are also provided, which may comprise a pharmaceutically acceptable carrier and/or excipient.

Other objects, advantages, and novel features of the invention will become more apparent from the following detailed description when taken in conjunction with the accompanying drawings.

BRIEF DESCRIPTION OF THE DRAWINGS

FIG. 1B is the amino acid sequence of human CD152 deduced from cDNA (Seq. ID No. 8) (Genebank accession number L15006, NCBI protein accession number P16410). Asterisks indicate the beginning of the mature peptide, transmembrane region and intracellular region. The CDR1, CDR2, and CDR3-like regions are boxed.

FIGS. 3A, 3B, 3C, 3D and 3E indicate results obtained from PHA stimulation alone (1.25, 5 and 20 μg/ml), 1.25 μg/ml of PHA with concomitant stimulation with cross-linking CD80 (0.2, 1 and 5 μg/ml), anti-CDR1, anti-CDR2 and anti-CDR3 antibodies (0.1, 1 and 10 μg/ml), respectively.

DETAILED DESCRIPTION OF THE PREFERRED EMBODIMENT

Figure 1A:
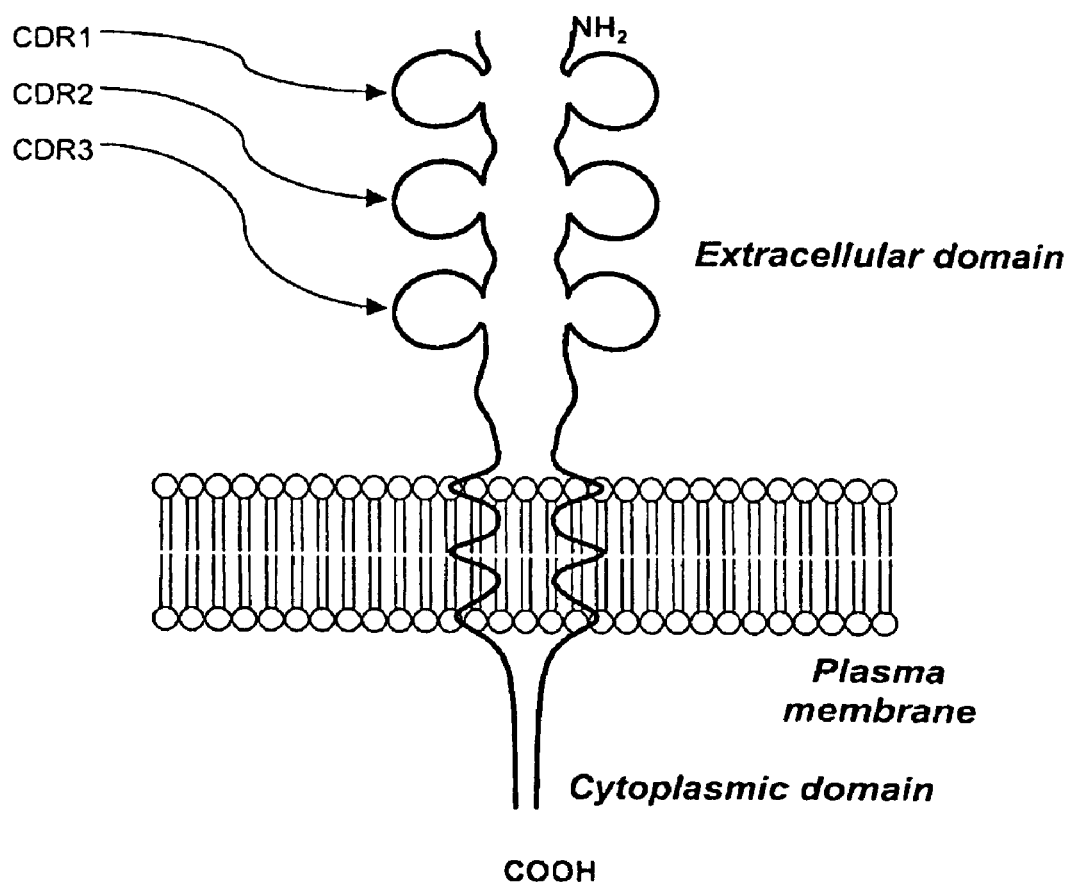
FIG. 1A is a schematic representation of homodimer configuration of CD152 receptor presented on the surface of a T cell. The relative locations of three immunoglobin CDR-like regions are indicated.
Figure 2:
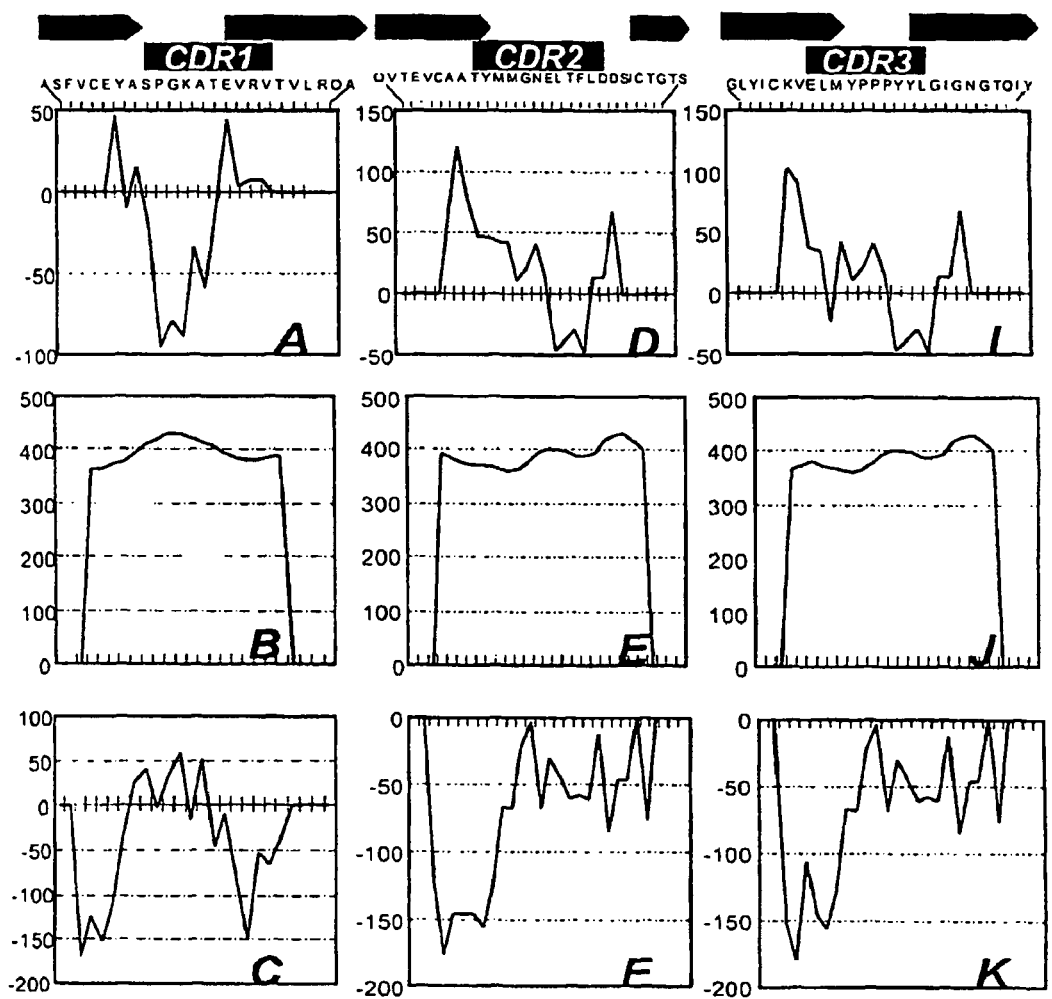
FIGS. 2A, 2B and 2C depict respectively hydrophobicity, chain flexibility and surface probability over the CDR1 and adjacent regions of human CD152.
FIGS. 2D, 2E and 2F illustrate respectively hydrophobicity, chain flexibility and surface probability over the CDR2 and adjacent regions.
FIGS. 2I, 2J and 2K scheme hydrophobicity, chain flexibility and surface probability over the CDR3 and adjacent regions, respectively. The boxed regions indicate CDR analogous regions with amino acids shown below. The arrows designate predicted strand structures derived from the corresponding residues.

The present invention provides methods of preparing fully human antibodies that recognize pharmacologic regions on a pre-determined receptor antigen without relying on human donors that have already been exposed to the antigen. To this end, possible immune active peptides are obtained first from the receptor of interest by using algorithms for epitope prediction and selection. Lymphocytes from naive human donors are immunized in vitro with peptide-based immunogens, and cells that produce antibodies against the receptor are identified and selected. Since the lymphocytes are immunized in vitro rather than in vivo, it is possible to control which antigen, or which part of the receptor, would be recognized by the antibody. A preferred receptor is human CD152, particularly the CDR regions of CD152.

Prior to describing the invention in further detail, the terms used in this application are defined as follows unless otherwise indicated.

A "ligand" is a compound that binds to another molecule, such as a receptor protein.

A "receptor" is a protein interacting with extracellular physiological signals and converting them into intracellular effects.

A "fully (complete) human antibody" is an antibody containing exclusively human sequences.

A "naive human donor" is a human who has not been exposed to an antigen of interest and serves as the source of immune cells or factors. A naive donor does not contain detectable circulating antibodies against the antigen of interest. Typically naïve human donors are healthy, regular blood donors who are consistently screened negative of anti-HIV antibodies.

"Immunize" a cell or an animal with an antigen refers to the action of exposing the cell or the animal to the antigen. The cell or animal can be immunized in any manner that leads to contact between the cell or the animal with the antigen.

"Site-directed in vitro immunization" is an in vitro lymphocyte stimulation process to achieve antibody response to a protein by using a fraction of the protein of interest. It is based on a synthetic heterotope immunogen, which is a peptide containing both T- and B-cell epitopes, that elicited a humoral immune response against the whole protein. Techniques of site-directed in vitro immunization are known in the art. For example, Chin et al., 1994 described the preparation, characterization and use of the technology.

"Treating or ameliorating" a disease or medical condition means reducing or eliminating the symptoms of the disease or medical condition, or slowing down the progress of the disease/medical condition. The reduction is preferably at least about 10%, more preferably at least about 20%, 30%, 40%, 50%, 60%, 70%, 80% or 90%.

"Preventing" a disease or medical condition means taking a measure in a subject who shows no symptoms of the disease or medical condition, wherein, as a result, the subject does not develop the disease/medical condition or develops the disease/medical condition to a lesser extent.

An "effective amount" is an amount of an agent that is sufficient to result in the intended effect. For example, for an antibody used to treat or ameliorate a disease, an effective amount is an amount of the antibody sufficient to reduce or eliminate the symptoms of the disease, or to slow down the progress of the disease.

An "agonist" is called when a ligand has the same or similar effect as another naturally occurring, endogenous ligand or group of ligands.

An "antagonist" is called when a ligand or drug counteracts the effect of an agonist.

An "inverse agonist" is a ligand, which produces an effect opposite to that of the agonist by occupying the same receptor.

"Receptor blockade" is the blocking of the effect of a natural endogenous ligand, e.g., hormone or neurotransmitter, at a cell-surface receptor by a pharmacological antagonist bound to the receptor.

A "sample" is an aliquot or a representative portion of a substance, material, or population. For example, a sample may be a sample of water, sewage, oil, sand, blood, biological tissue, urine or feces.

A "biological sample" is a sample collected from a biological subject, such as an animal, plant or microorganism.

This invention also includes pharmaceutical compositions that contain, as the active ingredient, one or more of the antibodies in combination with a pharmaceutically acceptable carrier or excipients. In preparing the compositions of this invention, the active ingredient/antibody is usually mixed with an excipient, diluted by an excipient or enclosed within such a carrier, which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of solutions (particularly sterile injectable solutions), tablets, pills, powders, lozenges, sachets, cachets, elixirs, suspensions, emulsions, syrups, aerosols (as a solid or in a liquid medium), ointments containing, for example, up to 10% by weight of the antibody, soft and hard gelatin capsules, suppositories, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The liquid forms in which the novel compositions of the present invention may be incorporated for administration orally or by injection include aqueous solutions (such as PBS), suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Other suitable formulations for use in the present invention can be found in *Remington's Pharmaceutical Sciences*.

The following examples are offered to illustrate this invention and are not to be construed in any way as limiting the scope of the present invention. For example, similar research effort can be aimed at other members of the CD28 receptor superfamily such as CD28 and its isoforms (CD28i), inducible costimulator (ICOS), B and T lymphocyte attenuator (BTLA) and programmed cell death 1 (PD-1). Likewise, application can also be made to other receptor families includes ion channels, G-protein coupled receptors, tyrosine kinase-linked receptors and transcription factors.

TABLE 1

Amino acid sequences of peptides in this invention

| Peptides | Amino acid sequence | SEQ ID No. |
|---|---|---|
| TT | N'—QYIKANSKFIGITEL—C' | 1 |
| CDR1 $_{(ext)}$ | N'—EYASPGKATEVRVTV—C' | 2 |
| CDR2 $_{(ext)}$ | N'—AATYMMGNELTFLDD—C' | 3 |
| CDR3 $_{(ext)}$ | N'—KVELMYPPPYYLGIG—C' | 4 |
| TT-CDR1 $_{(ext)}$ | N'—QYIKANSKFIGITELEYASPGKATEVRVTV—C' | 5 |
| TT-CDR2 $_{(ext)}$ | N'—QYIKANSKFIGITELAATYMMGNELTFLDD—C' | 6 |
| TT-CDR3 $_{(ext)}$ | N'—QYIKANSKFIGITELKVELMYPPPYYLGIG—C' | 7 |

Example 1

Preparation of Peptide Antigens

The overall structure of human CD152 protein receptor is represented schematically by FIG. 1A. Amino acid sequence corresponding to human CD152 is shown in FIG. 1B. By incorporating information gained from scientific literatures, the importance of the interrelationships between the CDR3 region and natural CD80 and CD86 ligands has been established. Further evidence suggests that residues locating in the CDR1 region play some role in interaction with CD80/CD86. However, the nature of CDR2 in agonist binding has not yet been fully investigated.

To raise an antibody that can bind native protein, the peptide should also adopt a conformation that mimics its shape when contained within the protein. Therefore, complete sequences derived from the respective CDR1, CDR2 and CDR3 regions are preserved for designing synthetic immunogens. Furthermore, extensions were made to each CDR peptide to comply the combined epitope model as previously described (Chin et al., Immunology 81:428, 1994; Chin et al., Eur. J. Immunol. 25:657, 1995). As an effective immunogen, the peptide must be selected from an accessible region of the protein if the resulting antibody is to be of use. The most accessible areas will be those parts of the molecule that are exposed or on the outside of the structure. As these regions are in contact with an aqueous environment they are usually hydrophilic. Hydrophobic plots were then established to determine the orientation of extension by using GeneWorks® software (IntelliGenetics, Mountain View, Calif.). Additionally, chain flexibility and surface probability, calculated by using GeneWorks®, over the adjacent regions were also taken into account as secondary parameters for peptide design (FIG. 2).

High scoring CDR peptides from the above stimulation were synthesized and used to prepare combined epitopes in conjugation with the "helper" sequence derived from tetanus toxin encompassing amino acids 830-844 (see peptide "TT", SEQ ID NO: 1). For example, to generate an immunogen containing both T-cell and B-cell epitopes, peptide "TT" was combined with an extended fragment of CDR1 of human CD152 (peptide "CDR1$_{(ext)}$", SEQ ID No:2) to form TT-CDR1$_{(ext)}$(SEQ ID No:5).

Example 2

Generation of Anti-CD152 Human Antibodies

Buffy coats from healthy blood donors, screened negative for HIV-1/2, HTLV-I/II, HCV, HBsAg and containing normal levels of alanine transferase (ALT), were obtained from the Tainan Blood Center, Chinese Blood Services Foundation (Tainan, Taiwan). Peripheral blood mononuclear cells (PBMC) were isolated by density centrifugation (400×g) on FICOLL-PAQUE™ (Amersham Biosciences AB, Uppsala, Sweden). The cells were then washed twice in PBS and collected by 100×g centrifugation.

The obtained PBMC were first magnetically labeled with CD45RO MACS™ microbeads (Miltenyi Biotec, Auburn Calif.) then separated by using a VarioMACS™ (Miltenyi Biotec) instrument. Briefly, the cells were specifically labeled with super-paramagnetic MACS™ microbeads. After magnetic labeling, the cells were passed through a separation column, which was placed in a strong permanent magnet. The magnetizable column matrix served to create a high-gradient magnetic field. The magnetically labeled cells were retained in the column and separated from the unlabeled cells, which passed through. After removal of the column from the magnetic field, the retained cells were eluted. The eluted CD45RO$^+$ cells were recovered by 100×g centrifugation and were used immediately. The CD45RO$^+$ T cells were cultured in tissue culture flasks at a density of $2\times10^6$ cells/ml in RPMI-1640 (HyQTM; HyClone, Logan, Utah) supplemented with 1× non-essential amino acids (Life Technologies, Grand Island, N.Y.), 10% human serum, 50 μg/ml gentamycin/kanamycin (China Chemical & Pharmaceutical, Taipei, Taiwan), 50 μM 2-mercaptoethanol and 10 μg/ml pokeweed mitogen (PWM; Sigma Chemicals). After 24 hr incubation, cells were spun down and removed by 400×g centrifugation. Finally, CD45RO$^+$ T cell replacing factor, i.e., culture supernatant, was prepared by harvesting the culture supernatant, filtering with a 0.45 mm filter, and stored frozen at −20° C.

Magnetic cell depletion was performed on PBMC to remove cytotoxic cell populations, which inhibit in vitro immunization. Colloidal super-paramagnetic microbeads conjugated to monoclonal anti-mouse CD8 and anti-CD56 antibodies (Miltenyi Biotech) were used as described above. Cytotoxic cell-depleted PBMC, were immunized in vitro using a two-step immunization protocol. Primary immunization was performed by incubating the cells for 6 days in a medium containing 10 nM of the peptide antigens, i.e., TT-CDR1$_{(ext)}$, TT-CDR2$_{(ext)}$ and TT-CDR3$_{(ext)}$ in media containing 50 μM 2-mercaptoethanol, 10% heat-inactivated human serum, 0.05 ng/ml rIL2 (Calbiochem, San Diego, Calif.), and 25% (v/v) CD45RO$^+$ T cell replacing factor. On day 7, cells from the primary immunization were harvested and spun through 40% FICOLL-PAQUE™. For secondary immunization, $3\times10^7$ cells were mixed with the peptide antigen in a flask that had been immobilized overnight with 5 μg/ml of CD40L (CD154; Vinci-Biochem, Vinci, Italy). The cells were cultured for 3-5 days in a medium supplemented with 5% human serum, 50 μM 2-mercaptoethanol and 10 nM peptide antigen.

The in vitro immunized cells were then infected with EBV. Briefly, $10^7$ lymphocytes were incubated for 2 hr at 37° C. with occasional resuspension with 1 ml EBV-containing supernatant derived from the EBV-producing marmoset cell line B95-8 (American Type Culture Collection, ATCC CRL 1612; kindly provided by Dr. L.-F. Shu, Tri Services General Hospital, Taipei). The infected cells were seeded at $10^5$/well in 96-well plates together with mytomycin (Kyowa Hakko Kogyo, Toyoko, Japan)-treated PBMC as feeder cells ($10^4$/well).

Antigen-specific ELISA was performed by first coating 1 μg/ml BHK cell-expressed recombinant human CD152 (CTLA-4)-muIg fusion protein (Ancell Corporation, Bayport, Minn.), 1 μg/ml monoclonal murine IgG2a (Ancell), 10 μg/well of bovine serum albumin (BSA; Sigma) or tetanus toxoid (ADImmune Corporation, Taichung, Taiwan) onto microtitre plates overnight at room temperature. Culture supernatants were diluted to the desired level in 10 mM sodium phosphate buffer, pH 8.0, containing 0 5 M sodium chloride and 0.1% Tween-20. Coated plates were incubated with diluted culture supernatants, washed, incubated with peroxidase-labeled goat antibodies against human IgG (Zymed Laboratories, So. San Francisco, Calif.) and developed (15 min) by addition of 100 μl of the chromogenic substrate o-phenylaenediamine (OPD) (Sigma). The reaction was stopped after 30 min by adding 1 M sulphuric acid, and the absorbances were read at 490 nm.

EBV-infected lymphoblastoid cells secreting putative anti-CD152 antibodies were identified by solid ELISA as described above. A well containing lymphoblastoid cells was scored as specific antibody-producing if:
(a) the ELISA OD value against recombinant human CD152-muIg fusion protein was at least five times as high as the OD value for the negative control;
(b) the reactivity index (RI) was >2, where RI= $[OD_{CD152\text{-}muIg}-OD_{medium\ control\ against\ CD152\text{-}muIg}]/[OD_{murine\ IgG2a}-OD_{medium\ control\ against\ murine\ IgG2a}]$.

Wells containing lymphoblastoid cells positive for the above assays were expanded and culture supernatants were collected, quantitated and standardized by ELISA for further study. The reactivity to the corresponding CDR region was confirmed by competitive ELISA using the respective peptide. These cultures were cloned by limiting dilution and cryopreserved.

Example 3

Anti-CD 152 Antibodies Varied in Their Ability to Induce Apoptosis and Proliferation as Compared with Native Agonist The binding sites of different anti-CD152 human antibodies were confirmed by corresponding synthetic peptides on primary alkyl amine derivatized cellulose membranes (Rapp Polymere GmbH, Tübingen, Germany). To further investigate the pharmacologic effect of different anti-CD152 antibodies and the preferred native agonist, CD80, on cellular growth of human peripheral lymphocytes stimulated in vitro by phytohemagglutinin (PHA), cultures of PBMC were established. Briefly, flat-bottomed 96-well microtitre plates were prepared by adding 50 μl of cell suspension ($10^5$ cells), 60 μl of medium containing PHA (final concentrations in culture 1.25 μg/ml, Amersham Biosciences AB), 40 μl of autologous plasma and 50 μl of RPMI-1640 medium containing anti-CD152 antibodies or monomeric human CD80-muIg fusion protein (Ancell) at concentrations ranging from 0.2 to 5 μg/ml. For CD80 stimulation, 5 μg/ml goat anti-mouse IgG2a (Southern Biotechnology Associates, Birmingham, Ala.) was added further to provide cross-linked forms of signals. The total culture volume was 200 μl. The cultures were incubated in a humidified atmosphere of 5% $CO_2$ in air at 37° C. for 96 h. Twenty hours before harvest, 50 μl of medium containing 0.5 μCi of tritiated thymidine (TRA 306, Amersham, specific activity 2 Ci/mol) was added to each well. Cultures were harvested on glass fiber filters with a semi-automatic multiple harvester (PHD, Cambridge Technology Inc.). Cell-bound [$^3$H]-thymidine was determined by counting in an LKB liquid scintillation counter. In some cultures, cell viability was measured at the end of the incubation period by the Trypan Blue dye exclusion test. Identical triplicate cultures were always performed and the median of each triplicate was used in the calculations.

The evaluation of the percentage of apoptosis, cells were centrifuged at 200×g, resuspended in cold 80% ethanol with vigorous mixing to a final density of $1\times10^6$/ml. The cells were incubated at 4° C. for a minimum of 30 min. The ethanol-fixed cells were then centrifuged and resuspended in 1 ml of the propidium iodide (PI; Sigma) staining reagent (PBS 0.15 M pH 7.4, 0.1% Triton X-100, 0.1 m M EDTA disodium salt, 50 μg/ml RNase A and 50 μg/ml PI). Samples were stored in the dark at room temperature until analysis, carried out within 24 h. The DNA content of cell nuclei was determined with propidium iodide staining and a FACScan™ cytometer using the Lysis II software (Becton Dickinson, Mountain View, Calif.). Apoptotic cells were determined by flow cytometry to measure the percentage of subdiploid DNA after propidium iodine staining.

Figure 3:
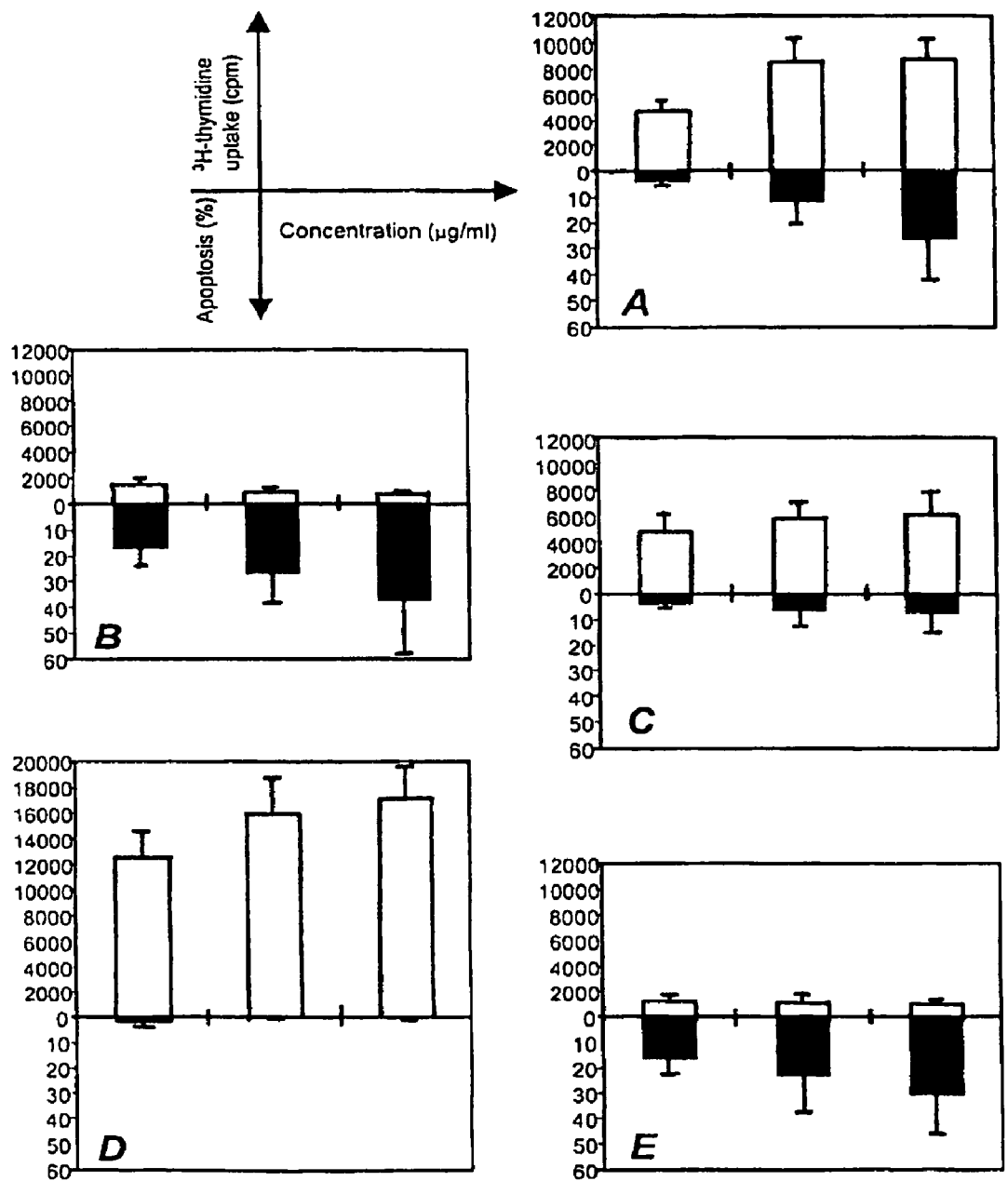
FIG. 3 shows representative reactivity profiles on proliferation (□) and apoptosis (■) of PHA-stimulated human PBMC.

We generated a panel of anti-CD152 human antibodies to determine the function of these ligands on human T cells activated by PHA, which yielded mediocre proliferation and apoptosis (FIG. 3A). Cross-linking CD80 induced apoptosis with no apparent proliferation observed (FIG. 3B). Similarly, antibodies induced by CDR3-containing peptide immunogen also provoked rapid cell death without proliferation, hence confirming an agonist activity (FIG. 3E). Stimulation with the CDR1-induced human antibodies significantly reduced, yet did not completely abolish, PHA-triggered cell death (FIG. 3C). Surprisingly, when PHA-activated PBMC were incubated with the CDR2-induced human antibodies alone, a high and reproducible cell proliferation was observed, and PHA-caused cell death was completely abolished (FIG. 3D). Cell proliferation induced on CD152 triggering by the anti-CDR2 was similar to that seen in 5 ng/ml IL-2-treated cultures and resulted in disappearance of the typical morphological alterations seen in apoptotic cells (e.g., membrane blebbing and disintegration of cells and nuclei into small vesicles).

Although the present invention has been explained in relation to its preferred embodiment, it is to be understood that many other possible modifications and variations can be made without departing from the spirit and scope of the invention as hereinafter claimed.

What is claimed is:

1. A method for preparing human antibodies recognizing a self physiological receptor, comprising following steps:
   (a) providing a group of lymphocytes obtained from a naïve human donor;
   (b) depleting CD56+ lymphocytes;
   (c) culturing said lymphocytes with in silico designed synthetic antigens encompassing amino acid sequence of self physiological receptor in vitro in the presence of CD40L;
   (d) adding Epstein-Barr virus (EBV) to the immunized lymphocytes; and
   (e) identifying EBV-infected cells that produce the antibody that recognizes the receptor.

2. The method of claim 1, wherein the resultant human antibodies are collected and screened for the presence of pharmacologic functions.

3. The method of claim 1, wherein the antigens are peptides comprising one or more Complementarity Determining Regions (CDRs) of Cytotoxic T-Lymphocyte Antigen 4(CD152), or an immunogenic fragment thereof.

4. The method of claim 3, wherein the antigens are peptides comprising one or more sequences selected from the group consisting of SEQ ID NOS: 2-4.

5. The method of claim 3, wherein the antigens are peptides comprising one CDR of CD152, or an immunogenic fragment thereof, and SEQ ID NO: 1.

6. The method of claim 3, wherein the antigens are peptides comprising one or more sequences selected from the group consisting of SEQ ID NOS: 5-7.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: tetanus toxin
<220> FEATURE:
<221> NAME/KEY: PEPTIDE
<222> LOCATION: (1)..(15)
<300> PUBLICATION INFORMATION:
<301> AUTHORS: Stephane Demotz, Antonio Lanzavecchia, Ulrich Eisel,
      Heiner Niemann, Christian Widmann, and Giampietro Corradin
<302> TITLE: Delineation of several dr-restricted tetanus toxin T cell
      epitopes
<306> PAGES: 394-402
<307> DATE: 1989-01-15
<313> RELEVANT RESIDUES: (1)..(15)

<400> SEQUENCE: 1
```

Gln Tyr Ile Lys Ala Asn Ser Lys Phe Ile Gly Ile Thr Glu Leu
1               5                   10                  15

<210> SEQ ID NO 2
<211> LENGTH: 15
<212> TYPE: PRT
<213> ORGANISM: Homo sapiens
<220> FEATURE:
<221> NAME/KEY: PEPTIDE
<222> LOCATION: (1)..(15)

<400> SEQUENCE: 2

Glu Tyr Ala Ser Pro Gly Lys Ala Thr Glu Val Arg Val Thr Val
1               5                   10                  15

<210> SEQ ID NO 3
<211> LENGTH: 15
<212> TYPE: PRT
<213> ORGANISM: Homo sapiens
<220> FEATURE:
<221> NAME/KEY: PEPTIDE
<222> LOCATION: (1)..(15)

<400> SEQUENCE: 3

Ala Ala Thr Tyr Met Met Gly Asn Glu Leu Thr Phe Leu Asp Asp
1               5                   10                  15

<210> SEQ ID NO 4
<211> LENGTH: 15
<212> TYPE: PRT
<213> ORGANISM: Homo sapiens
<220> FEATURE:
<221> NAME/KEY: PEPTIDE
<222> LOCATION: (1)..(15)

<400> SEQUENCE: 4

Lys Val Glu Leu Met Tyr Pro Pro Tyr Tyr Leu Gly Ile Gly
1               5                   10                  15

<210> SEQ ID NO 5
<211> LENGTH: 30
<212> TYPE: PRT
<213> ORGANISM: Artificial
<220> FEATURE:
<223> OTHER INFORMATION: CDR peptides were synthesized and used to
      prepare combined epitopes in conjugation with sequence "TT"
      derived from tetanus toxin.
<220> FEATURE:
<221> NAME/KEY: PEPTIDE
<222> LOCATION: (1)..(30)

<400> SEQUENCE: 5

Gln Tyr Ile Lys Ala Asn Ser Lys Phe Ile Gly Ile Thr Glu Leu Glu
1               5                   10                  15

Tyr Ala Ser Pro Gly Lys Ala Thr Glu Val Arg Val Thr Val
            20                  25                  30

<210> SEQ ID NO 6
<211> LENGTH: 30
<212> TYPE: PRT
<213> ORGANISM: Artificial
<220> FEATURE:
<223> OTHER INFORMATION: CDR peptides were synthesized and used to
      prepare combined epitopes in conjugation with sequence "TT"
      derived from tetanus toxin.
<220> FEATURE:
<221> NAME/KEY: PEPTIDE
<222> LOCATION: (1)..(30)

-continued

```
<400> SEQUENCE: 6

Gln Tyr Ile Lys Ala Asn Ser Lys Phe Ile Gly Ile Thr Glu Leu Ala
1               5                   10                  15

Ala Thr Tyr Met Met Gly Asn Glu Leu Thr Phe Leu Asp Asp
            20                  25                  30

<210> SEQ ID NO 7
<211> LENGTH: 30
<212> TYPE: PRT
<213> ORGANISM: Artificial
<220> FEATURE:
<223> OTHER INFORMATION: CDR peptides were synthesized and used to
      prepare combined epitopes in conjugation with sequence "TT"
      derived from tetanus toxin.
<220> FEATURE:
<221> NAME/KEY: PEPTIDE
<222> LOCATION: (1)..(30)

<400> SEQUENCE: 7

Gln Tyr Ile Lys Ala Asn Ser Lys Phe Ile Gly Ile Thr Glu Leu Lys
1               5                   10                  15

Val Glu Leu Met Tyr Pro Pro Tyr Tyr Leu Gly Ile Gly
            20                  25                  30

<210> SEQ ID NO 8
<211> LENGTH: 223
<212> TYPE: PRT
<213> ORGANISM: Homo sapiens
<220> FEATURE:
<221> NAME/KEY: PEPTIDE
<222> LOCATION: (1)..(223)
<300> PUBLICATION INFORMATION:
<308> DATABASE ACCESSION NUMBER: P16410
<309> DATABASE ENTRY DATE: 2004-03-15
<313> RELEVANT RESIDUES: (1)..(223)

<400> SEQUENCE: 8

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190
```

```
-continued

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```